United States Patent [19]

Axen et al.

[11] 4,337,338

[45] Jun. 29, 1982

[54] 2,5-INTER-O-PHENYLENE-3,4-DINOR-5,9α-EPOXY-6-IODO-PGF$_1$ AMIDES

[75] Inventors: Udo F. Axen, Plainwell; John C. Sih, Kalamazoo, both of Mich.

[73] Assignee: The Upjohn Company, Kalamazoo, Mich.

[21] Appl. No.: 165,835

[22] Filed: Jul. 3, 1980

Related U.S. Application Data

[60] Division of Ser. No. 62,443, Jul. 31, 1979, Pat. No. 4,312,810, which is a continuation-in-part of Ser. No. 962,845, Nov. 22, 1978, abandoned.

[51] Int. Cl.$^3$ .............................................. C07D 311/00
[52] U.S. Cl. .................................. 542/426; 542/429; 544/151; 544/376; 546/196; 546/269; 548/525; 260/330.9; 549/396

[58] Field of Search ..... 260/345.2, 326.36, 326.5 CA; 544/151, 376; 546/196, 269; 542/426, 429

[56] References Cited

U.S. PATENT DOCUMENTS 4,123,441 10/1978 Johnson ............................. 260/345.2

*Primary Examiner*—Nicky Chan
*Attorney, Agent, or Firm*—Robert A. Armitage

[57] ABSTRACT

The present invention provides 2,5-inter-o-phenylene-3,4-dinor-5,9α-epoxy-6-iodo-PGF$_1$ amides. These compounds are intermediates for preparing 2,5-inter-o-phenylene-3,4-dinor-prostacyclin analogs, which are useful for pharmacological purposes, e.g., as antithrombotic agents.

1 Claim, No Drawings

2,5-INTER-O-PHENYLENE-3,4-DINOR-5,9α-EPOXY-6-IODO-PGF$_1$ AMIDES

CROSS REFERENCE TO RELATED APPLICATION

This application is a division of Ser. No. 062,443 now U.S. Pat. No. 4,312,810, filed July 31, 1979, which is a continuation-in-part of Ser. No. 962,845, filed Nov. 22, 1978, now abandoned.

BACKGROUND OF THE INVENTION

The present invention relates to novel prostacyclin analogs and intermediates for their production. In particular, the present invention relates to prostacyclin intermediates useful in the production of 2,5-inter-o-phenylene-3,4-dinor-prostacyclin analogs. Most particularly the present invention provides 2,5-inter-o-phenylene-3,4-dinor-5,9α-epoxy-6-iodo-PGF$_1$ amides. The preparation and use of the novel compounds described herein is incorporated here by reference from U.S. Pat. No. 4,281,113.

SUMMARY OF THE INVENTION

The present invention particularly provides a prostacyclin intermediate of formula IX

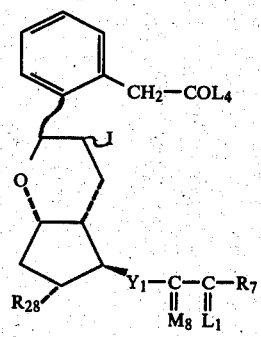

wherein $R_{28}$ is —$OR_{10}$, —$CH_2OR_{10}$, hydroxy, hydroxymethyl, or hydrogen, wherein $R_{10}$ is a blocking group removable by mild acidic hydrolysis;
wherein $Y_1$ is
(1) trans—CH=CH—,
(2) cis—CH=CH—,
(3) —$CH_2CH_2$—, or
(4) —C≡C—,
wherein $M_8$ is α-$R_5$:β-$OR_{10}$ or α-$OR_{10}$:β-$R_5$, wherein $R_5$ is hydrogen or methyl and $R_{10}$ is as defined above, or
α-$R_5$:β-OH or α-OH:β-$R_5$, wherein $R_5$ is as defined above;
wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $R_7$ is
(1) —$(CH_2)_m$—$CH_3$, wherein m is an integer from one to 5, inclusive;
(2) phenoxy;
(3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $L_4$ is
(1) amino of the formula —$NR_{21}R_{22}$, wherein $R_{21}$ and $R_{22}$ are
(a) hydrogen;
(b) alkyl of one to 12 carbon atoms, inclusive;
(c) cycloalkyl of 3 to 10 carbon atoms, inclusive;
(d) aralkyl of 7 to 12 carbon atoms, inclusive;
(e) phenyl;
(f) phenyl substituted with one, 2 or 3 chloro, alkyl of one to 3 carbon atoms, inclusive, hydroxy, carboxy, alkoxycarbonyl of one to 4 carbon atoms, inclusive, or nitro;
(g) carboxyalkyl of 2 to 5 carbon atoms, inclusive;
(h) carbamoylalkyl of 2 to 5 carbon atoms, inclusive;
(i) cyanoalkyl of 2 to 5 carbon atoms, inclusive;
(j) acetylalkyl of 3 to 6 carbon atoms, inclusive;
(k) benzoylalkyl of 7 to 11 carbon atoms, inclusive;
(l) benzoylalkyl substituted by one, 2 or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(m) pyridyl;
(n) pyridyl substituted by one, 2 or 3 chloro, alkyl of one to 3 carbon atoms, inclusive, or alkoxy of one to 3 carbon atoms, inclusive;
(o) pyridylalkyl of 6 to 9 carbon atoms, inclusive;
(p) pyridylalkyl substituted by one, 2 or 3 chloro, alkyl of one to 3 carbon atoms, inclusive, hydroxy or alkoxy of one to 3 carbon atoms, inclusive;
(q) hydroxyalkyl of one to 4 carbon atoms, inclusive;
(r) dihydroxyalkyl of one to 4 carbon atoms, inclusive, or
(s) trihydroxyalkyl of one to 4 carbon atoms, inclusive; with the further proviso that not more than one of $R_{21}$ and $R_{22}$ is other than hydrogen or alkyl; (2) cycloamino selected from the group consisting of
(a) pyrrolidino,
(b) piperidino,
(c) morpholino,
(d) piperazino,
(e) hexamethyleneimino,
(f) pyrrolino,
(g) 3,4-didehydropiperidinyl, or
(h) pyrrolidino, piperidino, morpholino, piperazino, hexamethyleneimino, pyrrolino, or 3,4- didehydropiperidinyl substituted by one or two alkyl of one to 12 carbon atoms, inclusive;
(3) carbonylamino of the formula $-NR_{23}COR_{21}$, wherein $R_{23}$ is hydrogen or alkyl of one to 4 carbon atoms and $R_{21}$ is other than hydrogen, but otherwise as defined above; or
(4) sulfonylamino of the formula $-NR_{23}SO_2R_{21}$, wherein $R_{21}$ and $R_{23}$ are as defined in (3).

The novel prostaglandin analogs prepared from the above intermediates are useful for a variety of prostacyclin-like pharmacological purposes, particularly and especially as inhibitors of platelet aggregation in vivo and in vitro. Thus, these prostacyclin analogs are useful for a variety of pharmacological and therapeutical purposes, e.g., as antithrombotic agents.

We claim:

1. A prostacyclin intermediate of formula IX

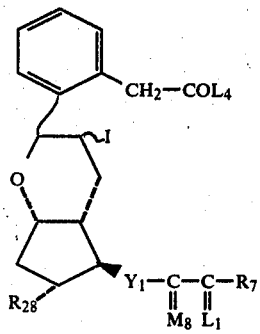

wherein $R_{28}$ is $-OR_{10}$, $-CH_2OR_{10}$, hydroxy, hydroxymethyl, or hydrogen, wherein $R_{10}$ is a blocking group removable by mild acidic hydrolysis;
wherein $Y_1$ is
(1) trans$-CH=CH-$,
(2) cis$-CH=CH-$,
(3) $-CH_2CH_2-$, or
(4) $-C\equiv C-$,
wherein $M_8$ is $\alpha$-Rhd $5:\beta$-$OR_{10}$ or $\alpha$-$OR_{10}:\beta$-$R_5$, wherein $R_5$ is hydrogen on methyl and $R_{10}$ is as defined above, or
$\alpha$-$R_5:\beta$-OH or $\alpha$-OH$:\beta$-$R_5$, wherein $R_5$ is as defined above;
wherein $L_1$ is $\alpha$-$R_3:\beta$-$R_4$, $\alpha$-$R_4:\beta$-$R_3$, or a mixture of $\alpha$-$R_3:\beta$-$R_4$ and $\alpha$-$R_4:\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $R_7$ is
(1) $-(CH_2)_m-CH_3$, wherein m is an integer from one to 5, inclusive;
(2) phenoxy;
(3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, 2 to 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;

wherein $L_4$ is
(1) amino of the formula $-NR_{21}R_{22}$, wherein $R_{21}$ and $R_{22}$ are
 (a) hydrogen;
 (b) alkyl of one to 12 carbon atoms, inclusive;
 (c) cycloalkyl of 3 to 10 carbon atoms, inclusive;
 (d) aralkyl of 7 to 12 carbon atoms, inclusive;
 (e) phenyl;
 (f) phenyl substituted with one, 2 or 3 chloro, alkyl of one to 3 carbon atoms, inclusive, hydroxy, carboxy, alkoxycarbonyl of one to 4 carbon atoms, inclusive; or nitro;
 (g) carboxyalkyl of 2 to 5 carbon atoms, inclusive;
 (h) carbamoylalkyl of 2 to 5 carbon atoms, inclusive;
 (i) cyanoalkyl of 2 to 5 carbon atoms, inclusive;
 (j) acetylalkyl of 3 to 6 carbon atoms, inclusive;
 (k) benzoylalkyl of 7 to 11 carbon atoms, inclusive;
 (l) benzoylalkyl substituted by one, 2 or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
 (m) pyridyl;
 (n) pyridyl substituted by one, 2 or 3 chloro, alkyl of one to 3 carbon atoms, inclusive, or alkoxy of one to 3 carbon atoms, inclusive;
 (o) pyridylalkyl of 6 to 9 carbon atoms, inclusive;
 (p) pyridylalkyl substituted by one, 2 or 3 chloro, alkyl of one to 3 carbon atoms, inclusive, hydroxy or alkoxy of one to 3 carbon atoms, inclusive;
 (q) hydroxyalkyl of one to 4 carbon atoms, inclusive;
 (r) dihydroxyalkyl of one to 4 carbon atoms, inclusive, or
 (s) trihydroxyalkyl of one to 4 carbon atoms, inclusive; with the further proviso that not more than one of $R_{21}$ and $R_{22}$ is other than hydrogen or alkyl;
(2) cycloamino selected from the group consisting of
 (a) pyrrolidino,
 (b) piperidino,
 (c) morpholino,
 (d) piperazino,
 (e) hexamethyleneimino,
 (f) pyrrolino,
 (g) 3,4-didehydropiperidinyl, or
 (h) pyrrolidino, piperidino, morpholino, piperazino, hexamethyleneimino, pyrrolino or 3,4-didehydropiperidinyl substituted by one or two alkyl of one to 12 carbon atoms, inclusive;
(3) carbonylamino of the formula $-NR_{23}COR_{21}$, wherein $R_{23}$ is hydrogen or alkyl of one to 4 carbon atoms and $R_{21}$ is other than hydrogen, but otherwise as defined above; or
(4) sulfonylamino of the formula $-NR_{23}SO_2R_{21}$, wherein $R_{21}$ and $R_{23}$ are as defined in (3).

* * * * *

UNITED STATES PATENT OFFICE
CERTIFICATE OF CORRECTION

Patent No. 4,337,338　　　　　　　　　Dated June 29, 1982

Inventor(s) Axen, U.F. and Sih, J.C.

It is certified that error appears in the above-identified patent and that said Letters Patent are hereby corrected as shown below:

Column 2, line 35 reads --acetyalkyl of-- should read "acetylalkyl of"

Column 3, line 42 reads --$\alpha$-Rhd 5:$\beta$-OR$_{10}$-- should read "$\alpha$-R$_5$:$\beta$-OR$_{10}$"

Column 3, line 43 reads --hydrogen on methyl-- should read "hydrogen or methyl"

Signed and Sealed this

Seventh Day of September 1982

[SEAL]

*Attest:*

*Attesting Officer*

GERALD J. MOSSINGHOFF

*Commissioner of Patents and Trademarks*